United States Patent
Ohtsuka et al.

(10) Patent No.: US 8,474,337 B2
(45) Date of Patent: Jul. 2, 2013

(54) EXTRACTION METHOD, EXTRACTION VESSEL FOR USE WITH THE SAME, EXTRACTION KIT AND VALVE EXPANSION MEMBER

(75) Inventors: Yuzuru Ohtsuka, Kanagawa-ken (JP); Akira Ito, Kanagawa-ken (JP); Mitsuaki Uchida, Kanagawa-ken (JP); Tomonori Nishio, Kanagawa-ken (JP); Katsuya Inana, Kanagawa-ken (JP); Yasunori Ohta, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 105 days.

(21) Appl. No.: 13/045,350

(22) Filed: Mar. 10, 2011

(65) Prior Publication Data

US 2011/0239793 A1 Oct. 6, 2011

(30) Foreign Application Priority Data

Mar. 31, 2010 (JP) .................................. 2010-083896

(51) Int. Cl.
*G01N 1/04* (2006.01)

(52) U.S. Cl.
USPC ...................................................... 73/864.71

(58) Field of Classification Search
None
See application file for complete search history.

(56) References Cited

U.S. PATENT DOCUMENTS

| | | | | |
|---|---|---|---|---|
| 4,539,855 A | * | 9/1985 | Jacobs | 73/864.25 |
| 4,746,614 A | | 5/1988 | Devaney, Jr. et al. | |
| 5,081,872 A | * | 1/1992 | Greter | 73/864.74 |
| 2006/0178568 A1 | * | 8/2006 | Danna et al. | 600/300 |
| 2008/0193926 A1 | * | 8/2008 | Abraham-Fuchs et al. | 435/6 |

FOREIGN PATENT DOCUMENTS

| | | |
|---|---|---|
| JP | 1-120276 (A) | 5/1989 |
| JP | 2005-300164 (A) | 10/2005 |
| JP | 2009-36732 A | 2/2009 |

OTHER PUBLICATIONS

Japanese Office Action dated Jan. 29, 2013, with English translation.

\* cited by examiner

*Primary Examiner* — Robert R Raevis
(74) *Attorney, Agent, or Firm* — McGinn Intellectual Property Law Group, PLLC

(57) ABSTRACT

A method is provided which is capable of efficiently taking most of a precious sample into an extraction vessel without wasting when the sample is extracted from a collection section of a sampling rod. The method includes the steps of collecting a sample using a sampling rod formed of a rod body and a collection section attached to the rod body, inserting the sampling rod into the extraction vessel, placing the rod body in a gap formed in a grappling hook section which is disposed in an insertion path of the sampling rod, the gap having a width smaller than a diameter of the collection section and being capable of receiving the rod body, withdrawing the rod body with the rod body being placed in the gap and detaching the collection section from the rod body by hooking the collection section to the grappling hook section.

4 Claims, 7 Drawing Sheets

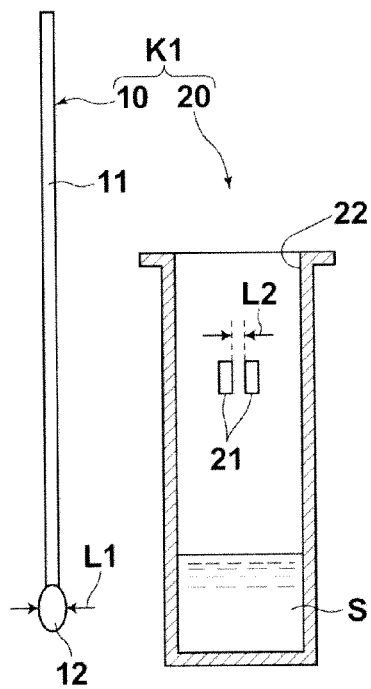
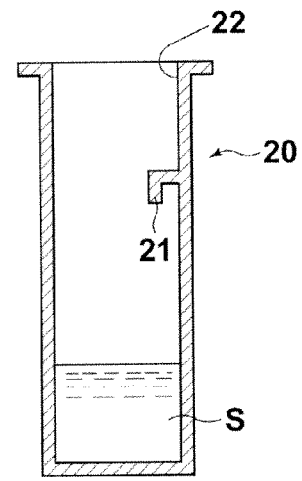
FIG.1A  FIG.1B
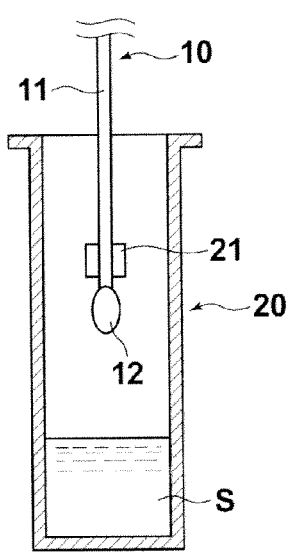
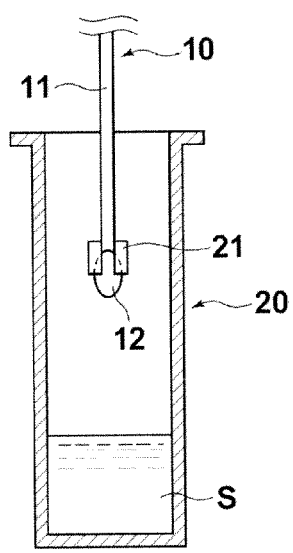
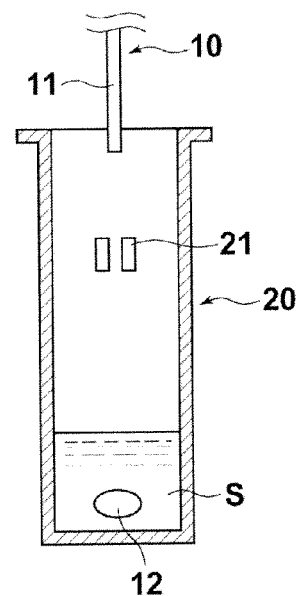
FIG.2A  FIG.2B  FIG.2C

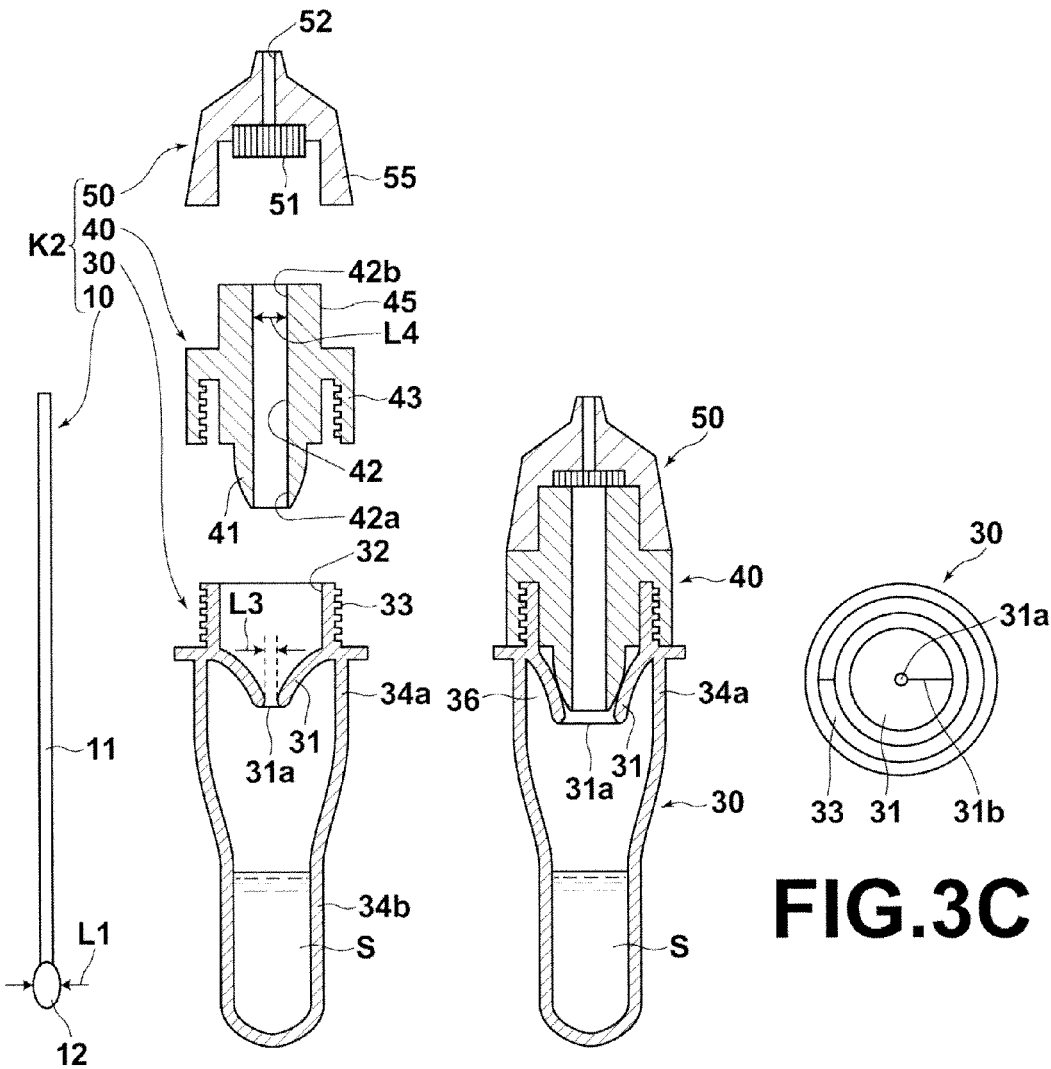
FIG.3A  FIG.3B  FIG.3C
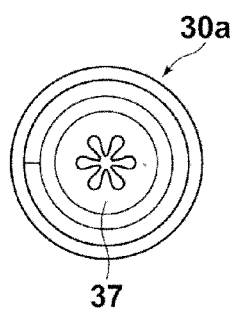 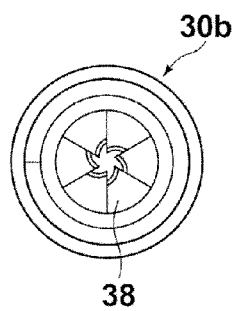 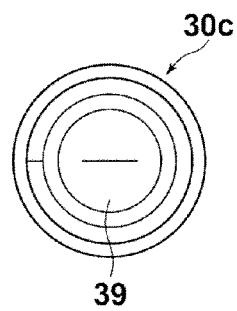
FIG.4A  FIG.4B  FIG.4C

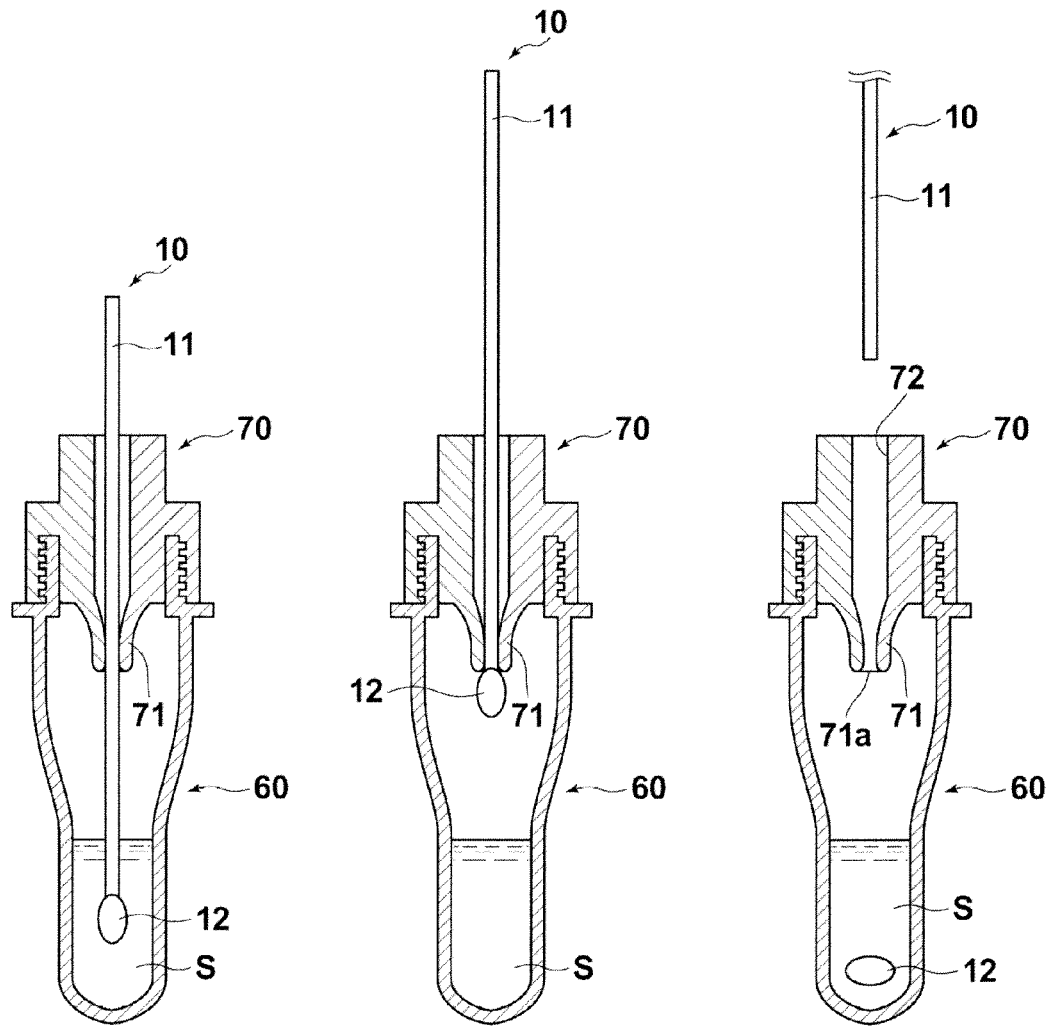

EXTRACTION METHOD, EXTRACTION VESSEL FOR USE WITH THE SAME, EXTRACTION KIT AND VALVE EXPANSION MEMBER

BACKGROUND OF THE INVENTION

1. Field of the Invention

The present invention relates to an extraction method for extracting a sample, such as blood, urine, sputum, saliva, nasal discharge, tear fluid, or feces collected by a sampling rod, from a collection section of the sampling rod, an extraction vessel used in the method, an extraction kit, and a valve expansion member.

2. Description of the Related Art

A method of testing a substance in a sample using an antigen-antibody reaction (immune reaction) or the like is widely applied to clinical examinations. For example, in a general test method using an antigen-antibody reaction, a test is performed in the following manner. That is, a sample, such as blood, urine, sputum, saliva, nasal discharge, tear fluid, feces, or the like, is collected using a sampling rod, such as a cotton swab, then the collected sample is extracted into a sample extraction solution in an extraction vessel, a sample solution in which the sample is extracted is brought into contact with a labeled antibody solution containing a labeled antibody labeled with a color identification substance, such as enzyme, noble metal colloid, colored latex, pigment, or the like to cause a specific reaction between the antigen in the sample and the labeled antibody for forming an antigen-antibody immune complex, and the amount of the immune complex is measured visually or as an optical change to perform a qualitative or quantitative measurement.

In the test method described above, an extraction vessel for extracting a sample from a collection section of the sampling rod is used in order to obtain a sample solution. For example, Japanese Unexamined Patent Publication No. 2009-036732 teaches a method for improving sample extraction efficiency by rubbing the swab of a cotton swab to which a sample is attached against a protrusion provided on an inner side wall of an extraction vessel.

In the method described in Japanese Unexamined Patent Publication No. 2009-036732, however, no matter how hardly the swab is rubbed against the protrusion, the extraction solution around the swab is absorbed again by the cotton swab when it is released from the compression. Thus, it causes a problem that a precious sample is wasted. The situation in which a sample reattached to a collection section of a sampling rod is discarded with the sampling rod is not limited to the case in which a test is performed using a cotton swab.

The amount of sample that can be obtained from a subject is limited and, therefore, it is desirable to use the collected sample efficiently without wasting as much as possible.

The present invention has been developed in view of the circumstances described above, and it is an object of the present invention to provide an extraction method, when extracting a sample collected by a sampling rod, such as a cotton swab or the like, from a collection section of the sampling rod, capable of taking most of the precious sample into an extraction vessel efficiently without wasting, an extraction vessel used in the method, and an extraction kit.

It is a further object of the present invention to provide a valve expansion member that allows, when a test is performed using an extraction vessel having a valve body with a valve opening having a diameter smaller than that of a collection section of a sampling rod and is capable of receiving a rod body of the sampling rod, easy insertion/extraction of the rod body of the sampling rod without attaching the sample to the valve body.

SUMMARY OF THE INVENTION

In order to solve the problem described above, an extraction method according to the present invention is a method, including the steps of:

collecting a sample using a sampling rod formed of a rod body and a collection section attached to the rod body;

inserting the sample rod into an extraction vessel;

placing the rod body in a gap formed in a grappling hook section which is disposed in an insertion path of the sampling rod, the gap having a width smaller than a diameter of the collection section and being capable of receiving the rod body;

withdrawing the rod body with the rod body being placed in the gap and detaching the collection section from the rod body by hooking the collection section to the grappling hook section;

immersing the detached collection section in an extraction solution contained in the extraction vessel.

The term of "insertion path of the sampling rod" as used herein refers to a space inside of the extraction vessel in which the sampling rod inserted from the opening is movable.

The term of "diameter of the collection section" as used herein refers to a maximum length of the collection section in a direction orthogonal to a length direction of the rod body.

The term of "gap having a width smaller than a diameter of the collection section" as used herein refers to a gap having a width smaller than the diameter of the collection section or, if the gap is scalable, it refers to a gap having a width smaller than the diameter of the collection section at a normal time (at a time of reduced diameter, for example, if the diameter is elastically scaled by an external force, the diameter without the external force. The same applies hereinafter). The term "a width of the gap" as used herein refers to a diameter of a maximum circle inscribed in the gap.

The term of the gap "being capable of receiving the rod body" as used herein refers to a gap having a width greater than a diameter of the rod body or a gap that may have a width greater than a diameter of the rod body by scaling. That is, where a gap can be scalable, it is not necessarily required that a width of the gap is greater than a diameter of the rod body at a normal time. The term of "diameter of the rod body" as used herein refers to a maximum length of the rod body in a direction orthogonal to a length direction of the rod body.

The term of "withdrawing the rod body with the rod body being placed in the gap" as used herein refers to withdrawing the rod body in a length direction of the rod body without changing the positional relationship between the rod body and the gap.

Preferably, in the extraction method of the present invention, the grappling hook section is a valve body disposed in the insertion path of the sampling rod inserted into the extraction vessel and provided with a valve opening having a normal time diameter smaller than the diameter of the collection section and being scalable; and after inserting the sampling rod into the valve opening, withdrawing, with the valve opening as the gap, the rod body with the rod body being placed in the valve opening and detaching the collection section from the rod body by hooking the collection section to the valve body.

The term of "normal time diameter" of the valve opening as used herein refers to a diameter of the opening (a diameter of a maximum circle inscribed in the opening) of the valve body viewed from the front (insertion path direction) under normal state.

The term of valve opening which is "scalable" as used herein refers to that the valve opening is expandable or reducible, for example, by an elastic property of the material of the valve body.

Preferably, in the extraction method of the present invention, that the sample is extracted while the detached collection section is unraveled.

An extraction vessel according to the present invention is a vessel for containing an extraction solution and extracting a sample, collected by a collection section of a sampling rod formed of a rod body and the collection section attached to the rod body, from the collection section into the extraction solution, the vessel having:

an opening; and a grappling hook section disposed in an insertion path of the sampling rod to be inserted from the opening and provided with a gap having a width smaller than a diameter of the collection section and being capable of receiving the rod body.

The term of "opening" of the extraction vessel as used herein refers to an opening section of an overall vessel. For example, if the vessel is formed of a plurality of members, it refers to an opening section of the vessel when all of the members are joined together.

Preferably, in the extraction vessel of the present invention, the grappling hook section is a valve body provided with a valve opening having a diameter smaller than the diameter of the collection section and being capable of receiving the rod body. Preferably, the valve body has a shape which becomes narrower toward the inner side of the vessel body.

Preferably, the extraction vessel of the present invention includes a vessel body for containing an extraction solution and a valve expansion member, wherein:

the vessel body is provided with a body opening and the valve body disposed in the insertion path of the sampling rod to be inserted from the body opening; and the valve expansion member is a member structured to be inserted into the body opening and fitted to the vessel body, and provided with a member opening, which is a through aperture that allows the sampling rod to be inserted into the vessel body when the member is fitted to the vessel body, and a valve expansion section that expands the valve opening when the member is fitted to the vessel body.

The term of valve expansion member is "fitted" to the vessel body as used herein refers to not only that an concave section and a convex section are fitted together so that the valve expansion member is inserted into the vessel body and operates on the valve body but also that the valve expansion member is joined to the vessel body by engaging the grappling hook section in an concave section (engagement) or by screwing (screw engagement).

Preferably, in the extraction vessel of the present invention, the valve expansion member is a member capable of adjusting a fitted depth of the member to the vessel body and structured to expand the valve opening further as the fitted depth is increased.

Alternatively, the extraction vessel of the present invention may include a vessel body for containing an extraction solution and a valve member, wherein:

the vessel body is provided with a body opening; and the valve member is a member structured to be inserted into the body opening and joined to the vessel body, and provided with a member opening, which is a through aperture that allows the sampling rod to be inserted into the vessel body when the member is joined to the vessel body, and the valve body disposed in the insertion path of the sampling rod to be inserted from the member opening.

The term of valve member is "joined" to the vessel body as used herein refers to not only that an concave section and a convex section are fitted together but also that the valve member is joined to the vessel body by engaging the grappling hook section in an concave section (engagement) or by screwing (screw engagement).

An extraction kit of the present invention is a kit, including:

the extraction vessel described above;

a sampling rod formed of a rod body and a collection section attached to the rod body and used for collecting a sample; and a lid member that can be joined to the opening of the extraction vessel, wherein:

the rid member includes a filter disposed at a position to close the opening when the lid member is joined to the opening and a nozzle section that allows the extraction solution to be taken outside through the filter when the lid member is joined to the opening.

A valve expansion member of the present invention is a member structured to be inserted into a body opening of a vessel body having the body opening and a valve body disposed in an insertion path of a sampling rod to be inserted from the body opening and containing an extraction solution, wherein:

the valve body is provided with a valve opening having a diameter smaller than a diameter of a collection section of the sampling rod and being capable of receiving a rod body of the sampling rod; and the valve expansion member is provided with a member opening, which is a through aperture that allows the sampling rod to be inserted into the vessel body when the member is fitted to the vessel body, and a valve expansion section that expands the valve opening when the member is fitted to the vessel body.

Preferably, the valve expansion member of the present invention is a member capable of adjusting a fitted depth of the member to the vessel body and structured to expand the valve opening further as the fitted depth is increased.

According to the extraction method of the present invention, a rod body of a sampling rod is placed in a gap formed in a grappling hook section which is disposed in an insertion path of the sampling rod, the gap having a width smaller than a diameter of the collection section and being capable of receiving the rod body, then the rod body is withdrawn with the rod body being placed in the gap and the collection section is detached from the rod body by hooking the collection section to the grappling hook section, and the detached collection section is immersed in an extraction solution contained in a vessel to extract a sample from the collection section. Thus, the collection section is not discarded and a sample reattached to the collection section is not wasted. Consequently, when a sample collected using a sampling rod, such as a cotton swab, is extracted from the collection section of the sampling rod, most of the precious sample can be taken in the extraction vessel efficiently without wasting.

The extraction vessel and the extraction kit according to the present invention include a grappling hook section disposed in an insertion path of the sampling rod and provided with a gap having a width smaller than a diameter of a collection section of the sampling rod and being capable of receiving the rod body. Therefore, the use of the extraction vessel and extraction kit allows the collection section to be detached from the sampling rod and the collection section is not discarded, so that a sample reattached to the collection section is not wasted. Consequently, when a sample collected using a sampling rod, such as a cotton swab, is extracted from the collection section of the sampling rod, most of the precious sample can be taken in the extraction vessel efficiently without wasting.

The valve expansion member of the present invention is structured to be inserted into a body opening of a vessel body disposed in an insertion path of a sampling rod to be inserted from the body opening, and containing an extraction solution, in which the valve body has a valve opening having a normal time diameter smaller than a diameter of a collection section of the sampling rod and being capable of receiving a rod body of the sampling rod and the valve expansion member has a member opening, which is a through aperture that allows the sampling rod to be inserted into the vessel body when the member is fitted to the vessel body, and a valve expansion section that expands the valve opening when the member is fitted to the vessel body. This allows the valve opening to be expanded simply by fitting the valve expansion member to the vessel body. Consequently, when a test is performed using an extraction vessel having a valve body provided with the valve opening described above, the rod body of the sampling rod can easily be inserted or extracted without the sample being attaching to the valve body.

BRIEF DESCRIPTION OF THE DRAWINGS

FIG. 1A is a schematic cross-sectional view of an extraction kit according to a first embodiment, illustrating the structure thereof.

FIG. 1B is a schematic cross-sectional view of the extraction kit according to the first embodiment taken along a cross-section passing through the grappling hook section.

FIGS. 2A to 2C are cross-sectional views, illustrating a process of detaching a swab in the first embodiment.

FIG. 3A is a schematic cross-sectional view of an extraction kit according to a second embodiment, illustrating the structure thereof.

FIG. 3B is a schematic cross-sectional view of the extraction kit according to the second embodiment, illustrating a state in which a vessel body, a valve expansion member, and a lid member are fitted together.

FIG. 3C is a schematic top view of the vessel body when the body opening is viewed from the top.

FIGS. 4A to 4C are schematic top views, illustrating alternative configurations of valve bodies provided in the extraction vessel of the present invention.

FIGS. 9A to 9C are schematic cross-sectional views, illustrating a process of detaching a swab in the third embodiment.

DESCRIPTION OF THE PREFERRED EMBODIMENTS

Figure 5:
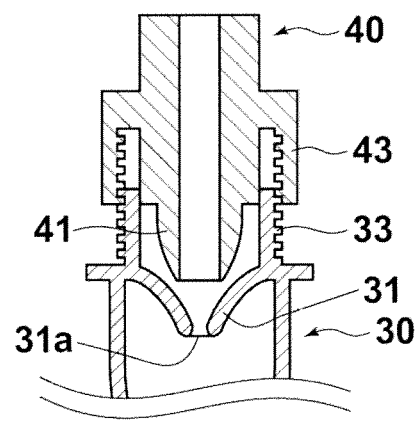
FIG. 5 is a schematic cross-sectional view, illustrating a positional relationship between the vessel body and the valve expansion member when they are shallowly fitted in the second embodiment.

Hereinafter, embodiments of the present invention will be described with reference to the accompanying drawings. But it should be appreciated that the invention is not limited to the embodiments described below. In the drawings, each component is not drawn to scale in order to facilitate visual recognition.

Extraction Method and Extraction Vessel of First Embodiment

First, an extraction method and an extraction vessel of a first embodiment of the present invention will be described. FIG. 1A is a schematic cross-sectional view of an extraction kit K1 having extraction vessel 20 of the present embodiment and cotton swab 10, and FIG. 1B is a schematic cross-sectional view of extraction vessel 20 taken along a cross-section passing through the grappling hook section. FIGS. 2A to 2C are schematic cross-sectional views, illustrating a swab detachment process in an extraction process using the extraction kit K1 of the present embodiment.

The extraction method of the present embodiment is a method, including the steps of obtaining a sample from a subject using cotton swab 10 having rod body 11 and swab 12 attached to rod body 11, inserting cotton swab 10 into extraction vessel 20 from opening 22 (FIG. 2A), placing rod body 11 in a gap L2 which is formed in grappling hook section 21 disposed in an insertion path of cotton swab 10 inside of extraction vessel 20, the gap having a width smaller than a diameter L1 of swab 12 and being capable of receiving rod body 11, withdrawing, after reasonably immersing swab 12 in an extraction solution S, rod body 11 with rod body 11 being placed in the gap L2 and detaching swab 12 from rod body 11 by grappling swab 12 to grappling hook section 21 (FIG. 2B), immersing detached swab 12 in the extraction solution S (FIG. 2C), and extracting the sample from swab 12 with cotton swab 12 remaining inside of extraction vessel 20.

Samples that can be used in the present invention include biological samples, such as urine, feces, saliva, nasal discharge, sputum, blood, serum, and the like, which are obtained by sampling rods, such as cotton swabs.

The term "extraction solution S" as used herein refers to a treatment liquid for making a sample appropriate for testing by being mixed in the sample, a diluting solution for diluting a sample, and a dispersion medium or a solvent for dispersing or dissolving a portion of a sample, as well as a liquid having a function to extract a particular component from a sample.

The term "extracting a sample" as used herein refers to dissolving or dispersing a sample or the like, which includes simply immersing a collection section that obtained a sample in an extraction solution to temporarily spread the sample or actively agitating, crushing, or unraveling the collection section immersed in the extraction solution.

In the mean time, the extraction kit K1 of the present embodiment includes cotton swab 10, formed of rod body 11 and swab 12 attached to rod body 11, and extraction vessel 20, as shown in FIG. 1A.

In the present embodiment, the sampling rod is cotton swab 10 but there is not any specific restriction on the sampling rod, and anything may be used as long as it is formed of a rod body and a collection section attached to the rod body, including those available in the market.

Generally, the sampling rod is formed of a collection section for collecting a sample by attachment, adsorption, or the like, and a rod body for supporting the collection section. There is not any specific restriction on the collection section and rod body. For example, the collection section may be made of a crumpled fiber material, such as cotton, rayon, nylon, polyester, pulp, hair (e.g., wool), silk, or the like, or a porous material formed in a predetermined shape, such as urethane, sponge (e.g., marine sponge), or the like. The rod body may be made of polypropylene, acrylic, polyacetal, wood, light metal (e.g., aluminum), or the like. Preferably, the collection section is made of cotton and rod body is made of rayon from the viewpoint of ease of sample collection and manufacturing. There is not any specific restriction on the shape of the collection section which is usually spherical or ellipsoidal, but the collection section may have a stepped uneven shape, a spiral shape, a tapered shape, or the like from the viewpoint of ease of sample collection. Preferably, the collection section has a diameter greater than the diameter of the rod body from the viewpoint of ease of sample correction and detachment, but it is not necessarily the case when a porous material is fixed to the tip of the rod body. There is not any specific restriction on the diameter of the collection section which is generally, for example, about 5 mm but ranges from 1 to 3 mm for babies to as large as about 10 mm. The length of the rod body is generally, for example, about 100 mm, but ranges from about 50 mm for babies to as long as about 150 to 200 mm. There is not any specific restriction on the method for attaching the collection section to the rod body and, for example, a method of winding a fiber material round the rod body, a method of fixing a porous material formed in a predetermined shape to the tip of the rod body, or the like may be used. It is necessary, however, that the collection section is attached to the rod body with a firmness level that does not detach the collection section when collecting a sample but detaches it if physical action is received from grappling hook section 21 when extracting the sample. The cotton swab used in the present embodiment is particularly preferable as the sampling rod because the swab becomes easily detachable when immersed in the extraction solution and wetted. The collection section is hooked to the grappling hook section and detached from the rod body, in which case the collection section may be detached together with a portion of the rod body (e.g., a core inserted in a porous material, which is formed in a predetermined shape, for fixing the porous material to the tip of the rod body) within an amount that does not influence the sample extraction.

Extraction vessel 20 has opening 22 and grappling hook section 21.

Grappling hook section 21 of the present embodiment is formed of two protrusions spaced apart so as to form a gap L2 in an insertion path of cotton swab 10 inside of extraction vessel 20. The gap L2 is designed to become larger than the diameter of rod body 11 of cotton swab 10 and smaller than a diameter L1 of swab 12. Thus, it is structured such that rod body 11 is allowed to slip through the gap L2 but swab 12 is hooked when cotton swab 10 is placed in the gap L2 and withdrawn. Therefore, if rod body 11 is withdrawn with swab 12 being hooked, swab 12 can be easily detached from rod body 11. In the present embodiment, grappling hook section 21 is formed of L-shaped protrusions, as illustrated in FIG. 1B, but the shape is not limited to this and the protrusions may have any other shapes. Further, a guide for guiding rod body 11 into the gap L2 may be provided by forming a slope at the corner of the protrusion.

Detached swab 12 is directly dropped into the extraction solution S, so that any known sample extraction process may be performed successively. There is not any specific restriction on the timing for detaching swab 12, but it is preferable that the detachment is performed after swab 12 is wetted reasonably in the extraction solution S and unraveled to a certain extent.

As described above, the extraction method according to the present embodiment is a method in which a rod body of a sampling rod is placed in a gap formed in a grappling hook section which is disposed in an insertion path of the sampling rod, the gap having a width smaller than a diameter of the collection section and being capable of receiving the rod body, then the rod body is withdrawn with the rod body being placed in the gap and the collection section is detached from the rod body by hooking the collection section to the grappling hook section, and the detached collection section is immersed in an extraction solution contained in a vessel to extract a sample from the collection section. Thus, the collection section is not discarded and a sample reattached to the collection section is not wasted. Consequently, when a sample collected using a sampling rod, such as a cotton swab, is extracted from the collection section of the sampling rod, most of the precious sample can be taken in the extraction vessel efficiently without wasting.

Further, the extraction vessel of the present embodiment includes a grappling hook section disposed in an insertion path of the sampling rod inserted from the opening and provided with a gap having a width smaller than a diameter of the collection section of a sampling rod and being capable of receiving the rod body. The use of the extraction vessel allows the collection section to be detached from the sampling rod and the collection section is not discarded, so that a sample reattached to the collection section is not wasted. Consequently, when a sample collected using a sampling rod, such as a cotton swab, is extracted from the collection section of the sampling rod, most of the precious sample can be taken in the extraction vessel efficiently without wasting.

Extraction Method, Extraction Vessel, and Extraction Kit of Second Embodiment

Next, an extraction method and an extraction kit of a second embodiment of the present invention will be described. FIG. 3A is a schematic cross-sectional view of the extraction kit K2 of the second embodiment, illustrating the structure thereof. FIG. 3B is a schematic cross-sectional view of the extraction kit K2 of the second embodiment, illustrating a state in which vessel body 30, valve expansion member 40, and lid member 50 are fitted together. FIG. 3C is a schematic top view of the vessel body 30 when body opening 32 is viewed from the top (insertion direction of the sampling rod).

The extraction method of the present embodiment is performed using the extraction kit K2 shown in FIG. 3A.

More specifically, the extraction method of the present embodiment is a method, including the steps of: proving an extraction vessel (30, 40) in which valve expansion member 40 is deeply fitted to vessel body 30 containing an extraction solution S; collecting a sample from a subject using cotton swab 10 formed of rod body 11 and swab 12 attached to rod body 11; inserting cotton swab 10 into the extraction vessel (30, 40) from opening 42; placing rod body 11 in valve opening 31a which is formed in valve body 31 disposed in an insertion path of cotton swab 10 inside of vessel body 30, the gap having a normal time diameter L3 smaller than a diameter L1 of swab 12 and being capable of receiving rod body 11, withdrawing, after reasonably immersing swab 12 in the extraction solution S, rod body 11 with rod body 11 being placed in valve opening 31a and detaching swab 12 from rod body 11 by hooking swab 12 to valve body 31, immersing detached swab 12 in the extraction solution S; and extracting the sample from swab 12 with swab 12 being taken in the extraction vessel (30, 40).

The extraction kit K2 of the present embodiment includes cotton swab 10, an extraction vessel formed of vessel body 30 and valve expansion member 40, and lid member 50 joined to valve expansion member 40, as illustrated in FIG. 3A.

Cotton swab 10 is identical to that of the first embodiment.

The extraction vessel of the present embodiment is structured such that valve expansion section 41 of valve expansion member 40 is inserted inside of vessel body 30 when vessel body 30 and valve expansion member 40 are fitted together.

Vessel body 30 has body opening 32, valve body 31 disposed in an insertion path of cotton swab 10 inserted from body opening 32, and screw-type body fitting section 33 for allowing valve expansion member 40 to be inserted in body opening 32 and fitted to vessel body 30. Vessel body 30 as a whole, including valve body 31, is an integrally molded resin product, but is formed such that area 34a of the side wall of vessel body on the opening side and area 34b on the bottom side have different hardness by differentiating the wall thickness or the like. In the present embodiment, area 34a of the side wall of vessel body on the opening side is formed relatively hard, while area 34b on the bottom side is formed to have a highly flexible property that allows elastic deformation. As for the elastically deformable material, any material which is elastic and flexible, and has chemical resistance and formability may be used and a non-odorous material is preferably used.

More specifically, elastically deformable materials may include, by way of example, thermoplastic resins, silicon resins, thermoplastic elastomers, and the like. Further, a combination of these resins may also be used. In the case of thermoplastic resins, and, for example, in the case of an olefin resin, it is known that the formability thereof is improved when combined with a hydrogenated styrene thermoplastic elastomer. The thermoplastic resins may include, by way of example, polyethylene, such as high-density polyethylene (HDPE), low-density polyethylene (LDPE), metallocene-catalyzed linear low-density polyethylene (L-LDPE), and the like, polypropylene, polyvinyl chloride, polystyrene, EVA, and the like. Further, a polymer blend or polymer alloy in which two or more of these are combined may be used. The thermoplastic elstomer is appropriately selected from styrene series, olefin series, urethane series, polyester series, polyamide series, fluorine series, vinyl chloride series, and the like in view of the formability, chemical resistance, environmental resistance, cost, and the like, in which styrene series and olefin series are preferable. They may be used singly or in combination, for example, by stacking or the like.

Valve body 31 is disposed in an insertion path of cotton swab inside of the vessel body (extraction vessel), and is provided with valve opening 31a having the normal time diameter L3 smaller than a diameter L1 of swab 12 and being capable of receiving rod body 11, thereby serving as the grappling hook section of the present invention. Provision of grappling hook section in the form of a valve body may provide a further advantageous effect of antiscattering or leakage of the sample or the extraction solution. Valve body 31 of the present embodiment is formed in a so-called check-valve shape in which it becomes narrower toward the inner side of vessel body 30 (extraction vessel). Slit 31b is formed in valve body 31 to facilitate opening/closing of valve opening 31a, as shown in FIG. 3C.

The valve body of the extraction vessel of the present invention is not limited to the embodiment described above and, for example, a valve body having an accordion shape, a valve body formed of a plurality of flaps, and a valve body having only a slit formed therein, as shown in FIGS. 4A to 4C respectively, may be also be used. Further, the valve body may be made of a brush-like material.

Valve expansion member 40 has member opening 42, which is a through aperture that allows cotton swab 10 to be inserted into vessel body when member 40 is fitted to vessel body 30, valve expansion section 41 that expands valve opening 31a when member 40 is fitted to vessel body 30, and fitting section 43 that allows member 40 to be fitted to vessel body 30.

Valve expansion section 41 is structured to push valve body 31 and expand valve opening 31a when valve expansion member 40 is deeply fitted to vessel body 30. This allows cotton swab 10 to be easily inserted/withdrawn even when a test is performed using vessel body 30 (extraction vessel) with valve opening 31a having the normal time diameter L3 smaller than a diameter L1 of swab 12 and being capable of receiving rod body 11.

Member opening 42 serves as the overall opening of the extraction vessel (vessel body 30 and valve expansion member 40) when valve expansion member 40 is fitted to vessel body 30. When they are fitted together, cotton swab 10 is inserted from member opening 42. There is not any specific restriction on the diameter L4 of member opening 42, but is preferable to be greater than the diameter L1 of swab 12 in order to facilitate insertion/withdrawal of cotton swab 10.

Member fitting section 43 is formed in a screw shape which is complementary to body fitting section 33 described above to allow valve expansion member 40 to be fitted to vessel body 30.

In the present embodiment, body fitting section 33 and member fitting section 43 are formed in screw so that a fitted depth of valve expansion member 40 to vessel body 30 can be adjusted by the screwing degree. The structure for adjusting the fitted depth of valve expansion member 40 to vessel body 30 is not limited to the screw structure for manual operation described above and, for example, a sliding structure or a structure in which the fitted depth is adjusted by a button may be employed. Valve expansion section 41 of the present embodiment is structured to further expand valve opening 31a as the fitted depth is increased. FIG. 5 is a schematic cross-sectional view, illustrating a state in which the fitted depth of valve expansion member 40 to vessel body 30 is shallow. In such a case, valve body 31 is not expanded because valve expansion section 41 is unable to touch valve body 31. In the present embodiment, both valve body 31 and valve expansion section 41 have taper shapes, but only either one of valve body 31 and valve expansion section 41 has a taper shape as the structure for adjusting the opening of valve opening 31a.

Lid member 50 includes filter 51 and nozzle 52, and joint section 55 is formed so that lid member is joined to outside portion 42b (opening of extraction vessel) of member opening 42 of valve expansion member 40. Filter 51 is disposed at a position to close opening 42b when lid member 50 is joined to opening 42b, and nozzle 52 allows the extraction solution S to be filtered and taken outside through filter 51 when lid member 50 is joined to opening 42b. By joining lid member 50 to the extraction vessel, the extraction solution S can be easily taken out to a test device, such as an immunochromatographic carrier, by directing nozzle 52 downward. In such a case, swab 12 remaining in the extraction vessel is blocked by filter 51 of lid member 50, thereby causing no influence on the test. The structure shown in FIGS. 3A to 3C may possible cause a problem that a portion of the extraction solution S is retained in space 36 between valve body 31 and side wall portion 34a of vessel body 30 and a required amount of the extraction solution S can not be taken out. But, this problem may be solved by providing an outlet in valve body 31 and valve expansion section 41.

A specific process of detaching swab 12 in the extraction method of the present embodiment will now be described with reference to FIGS. 6A to 6E.

Figure 6:
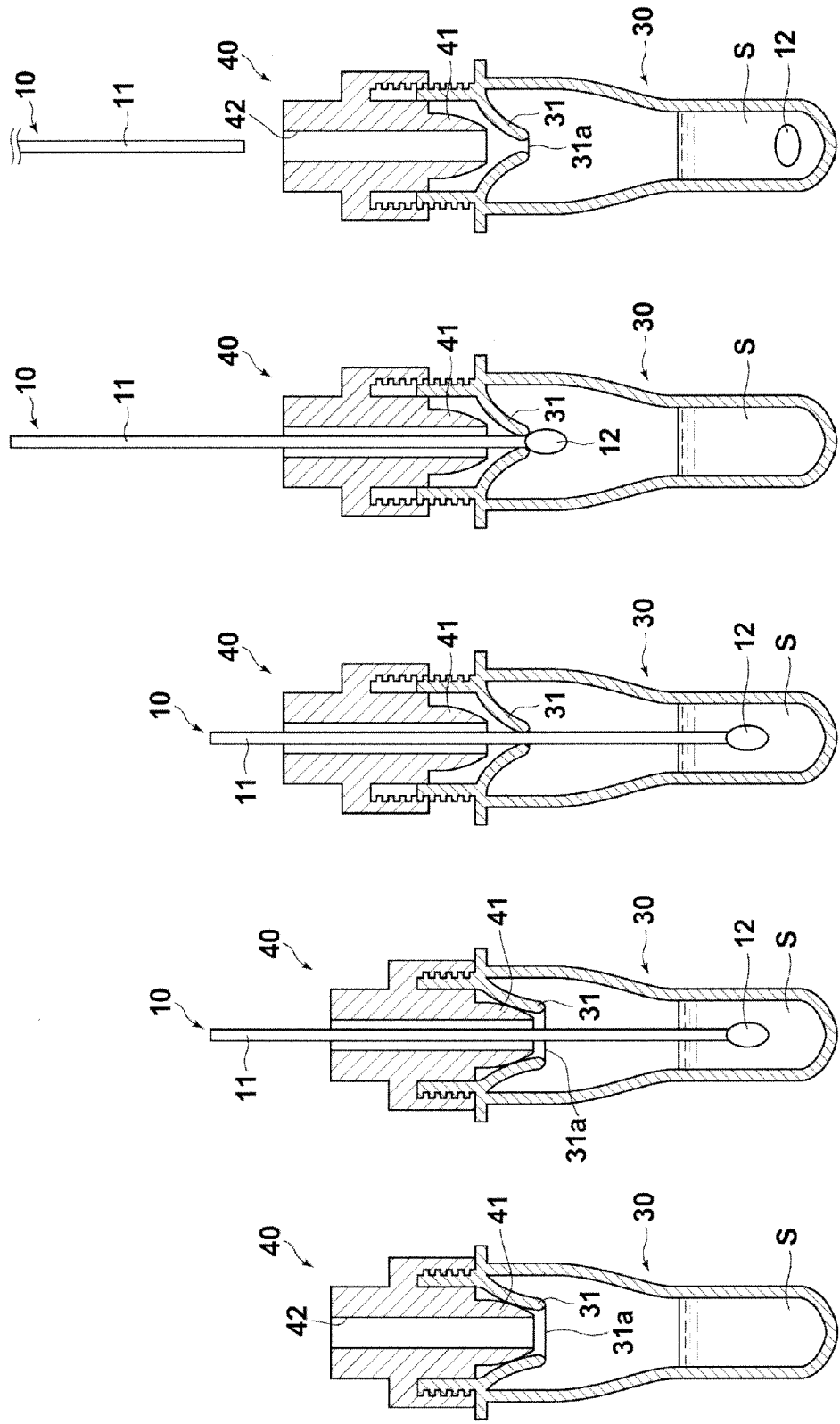
FIGS. 6A to 6E are schematic cross-sectional views, illustrating a process of detaching a swab in the second embodiment.

First, an extraction vessel formed of vessel body 30 and valve expansion member 40 fitted to vessel body 30 is provided (FIG. 6A). Here, valve expansion member 40 is fitted deeply to vessel body 30 so as to expand valve opening 31a. Cotton swab 10 having a collected sample thereon is inserted into the opening of the extraction vessel (member opening 42 of valve expansion member 40) and immersed into an extraction solution S (FIG. 6B). Thereafter, the expanded state of valve opening 31a is released by decreasing the fitted depth of valve expansion member 40 to vessel body 30 (FIG. 6C). Then, swab 12 is hooked to opening 31a of valve body 31 (FIG. 6D), and swab 12 is detached from rod body 11 by withdrawing rod body 11 (FIG. 6E). The process described above allows a precious sample to be taken in the extraction vessel efficiently without wasting.

Figure 7:
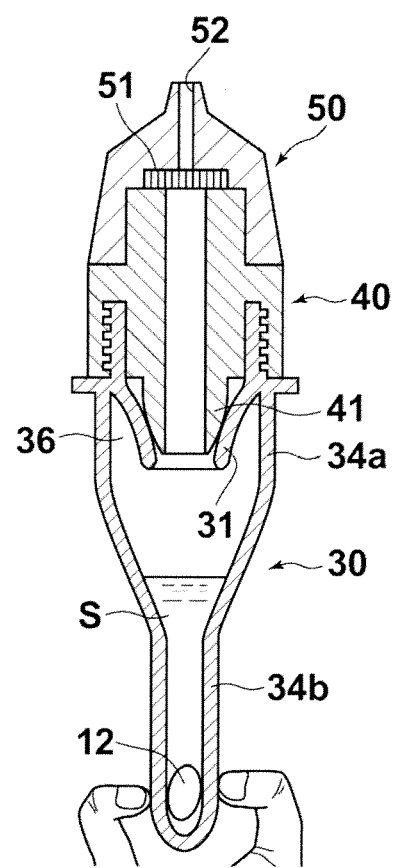
FIG. 7 is a schematic cross-sectional view, illustrating a state in which a sample is extracted from the detached swab while the swab is unraveled in the second embodiment.

For example, when taking out the extraction solution S using lid member 50, it is preferable to squeeze out the sample by pinching swab 12 over vessel body 30. It is also preferable to unravel swab 12 before taking out the extraction solution S, as illustrated in FIG. 7. This allows a portion of the sample, which is present deep in swab 12 and difficult to extract by simply taking swab 12 inside of the extraction vessel, to be extracted, whereby sample extraction efficiency is improved.

As described above, the extraction method according to the present embodiment is a method in which a rod body of a sampling rod is placed in a gap formed in a grappling hook section which is disposed in an insertion path of the sampling rod, the gap having a width smaller than a diameter of the collection section of the sampling rod and being capable of receiving the rod body, then the rod body is withdrawn with the rod body being placed in the gap and the collection section is detached from the rod body by hooking the collection section to the grappling hook section, and the detached collection section is immersed in an extraction solution contained in a vessel to extract a sample from the collection section. Thus, the collection section is not discarded and a sample reattached to the collection section is not wasted. Consequently, advantageous effects identical to those of the first embodiment may be obtained.

Further, the extraction method of the present embodiment uses a valve body disposed in an insertion path of a sampling rod and provided with a valve opening having a normal time diameter smaller than a diameter of the collection section and being capable of receiving the rod body as the grappling hook section. This may provide a further advantageous effect of antiscattering or leakage of the sample or the extraction solution.

Still further, in the extraction method of the present embodiment, the sample is extracted while the detached collection section is unraveled, so that a portion of the sample, which is present deep in the collection section and difficult to extract, can be extracted, whereby sample extraction efficiency is improved.

The extraction vessel and extraction kit of the present invention include a grappling hook section disposed in an insertion path of the sampling rod and provided with a gap having a width smaller than a diameter of a collection section of the sampling rod and being capable of receiving the rod body. Therefore, the use of the extraction vessel and extraction kit allows the collection section to be detached from the sampling rod and the collection section is not discarded, so that a sample reattached to the collection section is not wasted. Consequently, advantageous effects identical to those of the first embodiment may be obtained.

The extraction vessel and extraction kit of the present embodiment includes a valve body disposed in an insertion path of a sampling rod and provided with a valve opening having a normal time diameter smaller than a diameter of the collection section and being capable of receiving the rod body, as the grappling hook section. This may provide a further advantageous effect of antiscattering or leakage of the sample or the extraction solution.

Further, the extraction vessel and extraction kit of the present embodiment include a vessel body for containing an extraction solution and a valve expansion member, in which the vessel body is provided with a body opening and the valve body disposed in an insertion path of a sampling rod inserted from the body opening, while the valve expansion member is structured to be inserted into body opening and fitted to the vessel body, and is provided with a member opening, which is a through aperture that allows a sampling rod to be inserted into the vessel body when fitted to vessel body, and a valve expansion section that expands the valve opening when fitted to vessel body. Consequently, a sampling rod may be easily inserted/withdrawn even when a test is performed using a vessel body having the valve body with the valve opening like that described above.

Still further, in the extraction vessel and extraction kit of the present embodiment, the fitted depth of the valve expansion member to the vessel body can be adjusted and the valve expansion member is structured to further expand the valve opening as the fitting depth is increased, whereby opening/closing of the valve body can be performed easily.

Extraction Method, Extraction Vessel, and Extraction Kit of Third Embodiment

Figure 8A:
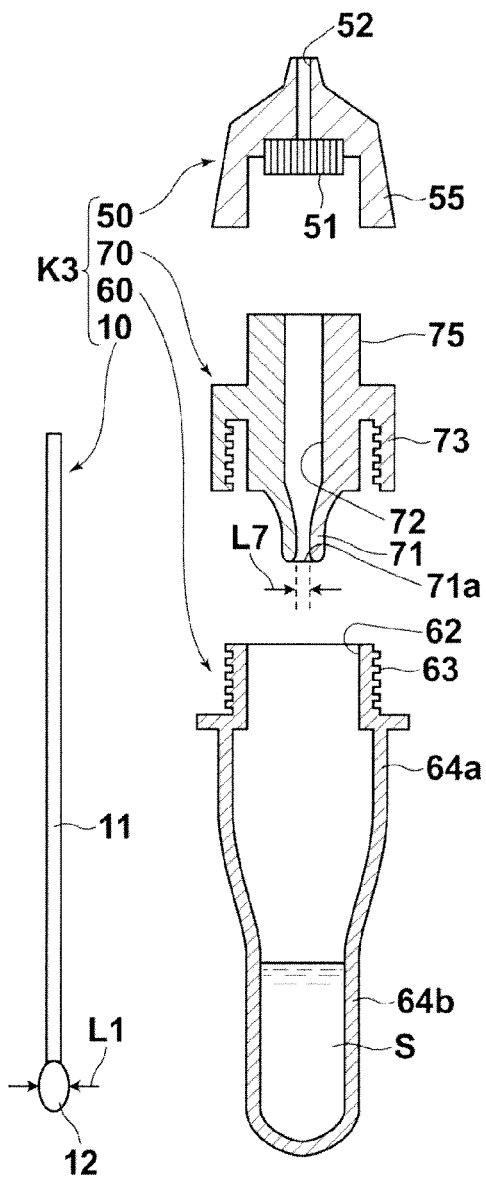
FIG. 8A is a schematic cross-sectional view of an extraction kit according to a third embodiment, illustrating the structure thereof.
Figure 8B:
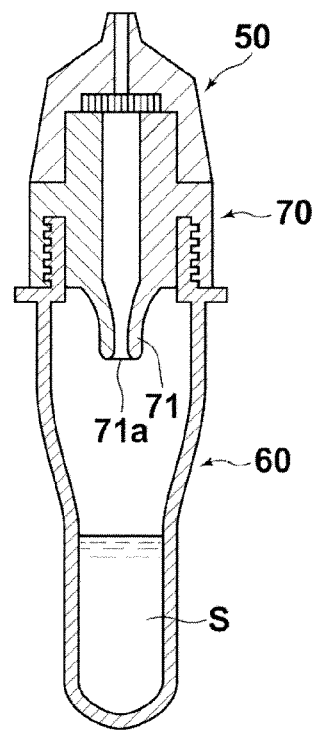
FIG. 8B is a schematic cross-section view of the extraction kit according to the third embodiment, illustrating a state in which a vessel body, a valve member, and a lid member are joined together.

Next, an extraction method and an extraction kit of a third embodiment of the present invention will be described. FIG. 8A is a schematic cross-sectional view of the extraction kit K3 of the second embodiment, illustrating the structure thereof. FIG. 8B is a schematic cross-sectional view of the extraction kit K3 of the third embodiment, illustrating a state in which vessel body 60, valve member 70, and lid member 50 are fitted together.

The extraction method of the present embodiment is performed using the extraction kit K3 shown in FIG. 8A.

More specifically, the extraction method of the present embodiment is a method, including the steps of: proving an extraction vessel (60, 70) formed of vessel body 60 containing an extraction solution S and valve member 70 joined to vessel body 60; collecting a sample from a subject using cotton swab 10 formed of rod body 11 and swab 12 attached to rod body 11; inserting cotton swab 10 into the extraction vessel (60, 70) from opening 72; placing rod body 11 in valve opening 71a which is formed in valve body 71 disposed in an insertion path of cotton swab 10 in valve member 70, the valve opening 71a having a normal time diameter L7 smaller than a diameter L1 of swab 12 and being capable of receiving rod body 11, withdrawing, after reasonably immersing swab 12 in the extraction solution S, rod body 11 with rod body 11 being placed in valve opening 71a and detaching swab 12 from rod body 11 by hooking swab 12 to valve body 71, immersing detached swab 12 in the extraction solution S; and extracting the sample from swab 12 with swab 12 being taken in the extraction vessel (60, 70)

The extraction kit K3 of the present embodiment includes cotton swab 10, an extraction vessel formed of vessel body 60 and valve member 70, and lid member 50 joined to valve member 70, as illustrated in FIG. 8A.

Cotton swab 10 is identical to that of the first embodiment and lid member 50 is identical to that of the second embodiment.

In the extraction vessel of the present embodiment, vessel body 60 and valve member 70 are joined such that valve body 71 of valve member 70 is inserted inside of vessel body 60.

Vessel body 60 has body opening 62 and screw-type body joining section 63 for allowing valve member 70 to be inserted in body opening 62 and joined to vessel body 60. Vessel body 60 as a whole is an integrally molded resin product but is formed such that area 64a of the side wall of vessel body 60 on the opening side and area 64b on the bottom side have different hardness by differentiating the wall thickness or the like, as in the second embodiment. The forming method and material of vessel body 60 are identical to those of the second embodiment.

Valve member 70 has member opening 72, which is a through aperture that allows cotton swab 10 to be inserted into vessel body 60 when joined to vessel body 60, valve body 71 disposed in an insertion path of cotton swab 10 to be inserted from member opening and provided with a valve opening 71a having a normal time diameter L7 smaller than a diameter L1 of swab 12 and being capable of receiving rod body 11, and joining section 73 that allows member 70 to be joined to vessel body 60. Materials usable for valve member 70 may include rubber, paper material, acrylic, rayon, urethane, thin-film metal, in addition to those used for vessel body 60.

Valve body 71 is provided on the vessel body side of member opening 72 of valve member 70 (corresponding to an insertion path of cotton swab 10 inside of the extraction vessel) and is provided with valve opening 71a having a normal time diameter L7 smaller than a diameter L1 of swab 12 and being capable of receiving rod body 11, thereby functioning as the grappling hook section of the present invention. Other aspects of the valve body 71 are identical to those of the valve body in the second embodiment.

Member opening 72 serves as the overall opening of the extraction vessel (vessel body 60 and valve member 70) when valve member 70 is joined to vessel body 60. When they are joined together, cotton swab 10 is inserted from member opening 72. There is not any specific restriction on the diameter of member opening 72, but is preferable to be greater than the diameter L1 of swab 12 in order to facilitate insertion/withdrawal of cotton swab 10.

Member joining section 73 is formed in a screw shape which is complementary to body joining section 63 described above to allow valve member 70 to be joined to vessel body 60. Valve member 70 does not require a function to adjust the fitted depth, so that valve member 70 is not necessarily joined so as to be inserted inside of vessel body 60, as illustrated in FIG. 8B.

A specific process of detaching swab 12 in the extraction method of the present embodiment will now be described with reference to FIGS. 9A to 9C.

First, an extraction vessel formed of vessel body 60 and valve member 70 joined to vessel body 60 is provided. Cotton swab 10 having a collected sample thereon is inserted into the opening of the extraction vessel (member opening 72 of valve member 70) and immersed into an extraction solution S (FIG. 9A). Thereafter, swab 12 is hooked to opening 71a of valve body 71 (FIG. 9B), and swab 12 is detached from rod body 11 by withdrawing rod body 11 (FIG. 9C) The process described above allows a precious sample to be taken in the extraction vessel efficiently without wasting.

As described above, by unraveling the detached swab 12, a portion of the sample, which is present deep in the swab 12 and difficult to extract by simply taking swab 12 inside of the extraction vessel, can be extracted, whereby sample extraction efficiency is improved.

As described above, the extraction method according to the present embodiment is a method in which a rod body of a sampling rod is placed in a gap formed in a grappling hook section which is disposed in an insertion path of the sampling rod, the gap having a width smaller than a diameter of a collection section of the sampling rod and being capable of receiving the rod body, then the rod body is withdrawn with the rod body being placed in the gap and the collection section is detached from the rod body by hooking the collection section to the grappling hook section, and the detached collection section is immersed in an extraction solution contained in a vessel to extract a sample from the collection section. Thus, the collection section is not discarded and a sample reattached to the collection section is not wasted. Consequently, advantageous effects identical to those of the first embodiment may be obtained.

The extraction vessel and extraction kit of the present invention include a grappling hook section disposed in an insertion path of the sampling rod and provided with a gap having a width smaller than a diameter of a collection section of the sampling rod and being capable of receiving the rod body. Therefore, the use of the extraction vessel and extraction kit allows the collection section to be detached from the sampling rod and the collection section is not discarded, so that a sample reattached to the collection section is not wasted. Consequently, advantageous effects identical to those of the first embodiment may be obtained.

Further, the extraction vessel and extraction kit of the present embodiment include a valve member structured to be joined to the vessel body and provided with a member opening, which is a through aperture that allows a sampling rod to be inserted into the vessel body when the valve member is joined to the vessel body, and a valve body disposed in an insertion path of the sampling rod to be inserted from the member opening and provided with a valve opening having normal time diameter smaller than a diameter of the collection section of the sampling rod and being capable of receiving the rod body. This allows the extraction method of the present invention to be easily applied to a vessel without a valve body and, when extracting a sample collected with a sampling rod, such as a cotton swab or the like, most of the precious sample can be taken in an extraction vessel efficiently without wasting.

What is claimed is:

1. An extraction vessel for containing an extraction solution and extracting a sample, collected by a collection section of a sampling rod comprising a rod body and the collection section attached to the rod body, from the collection section into the extraction solution, the vessel comprising:
   a vessel body for containing an extraction solution and a valve expansion member,
   wherein the vessel body is provided with a body opening and a valve disposed in an insertion path of the sampling rod to be inserted from the body opening, the valve being provided with a valve opening having a diameter smaller than a diameter of the collection section and being capable of receiving the rod body, and
   wherein the valve expansion member comprises a member structured to be inserted into the body opening and fitted to the vessel body, and provided with a member opening, which comprises a through aperture that allows the sampling rod to be inserted into the vessel body when the member is fitted to the vessel body, and a valve expansion section that expands the valve opening when the member is fitted to the vessel body.

2. The extraction vessel of claim 1, wherein the valve has a shape which becomes narrower toward an inner side of the vessel body.

3. The extraction vessel of claim 1, wherein the valve expansion member comprises a member capable of adjusting a fitted depth of the member to the vessel body and structured to expand the valve opening further as the fitted depth is increased.

4. An extraction kit, comprising:
the extraction vessel of claim 1;
a sampling rod comprising a rod body and a collection section attached to the rod body and used for collecting a sample; and
a lid member that is attachable to the extraction vessel, wherein the lid member includes a filter disposed at a position to close an opening when the lid member is joined to the opening and a nozzle section that allows the extraction solution to be taken outside through the filter when the lid member is joined to the opening.

\* \* \* \* \*